United States Patent [19]

Sakaki et al.

[11] Patent Number: 4,976,775

[45] Date of Patent: Dec. 11, 1990

[54] PLANT MALE STERILANT

[75] Inventors: Masaharu Sakaki, Toyonaka; Hiroko Yamazaki, Osaka, both of Japan

[73] Assignee: Sumitomo Chemical Company, Limited, Osaka, Japan

[21] Appl. No.: 318,203

[22] Filed: Mar. 3, 1989

[51] Int. Cl.$^5$ .................. A01N 37/20; A01N 37/18; A01N 33/26; A01N 33/04; A01N 33/08; A01N 33/02

[52] U.S. Cl. ..................... 71/106; 71/111; 71/113; 71/115; 71/118; 71/119

[58] Field of Search .................. 71/113, 106, 111, 115, 71/118, 119

[56] References Cited

U.S. PATENT DOCUMENTS 4,367,344  1/1983  Gallenkamp ................ 71/113

OTHER PUBLICATIONS

Journal of American Chemical Society, vol. 78, pp. 2423 to 2430, (1956).
Tetrahedron, vol. 39, pp. 475–478, (1983).
State of the Art, Strauss et al., "Application of the Disk Method to Cultured Plant Cells . . . ", Chem. Abstracts 101:106901p, 1984.
Schaeffer et al., *Increased Lysine and Seed Storage Protein in Rice* . . . , Chemical Abstract of Plant Physiol. 1987, 84(2), 509–15.
Bright et al., *The Effect of Aspartate-Derived Amino Acids* . . . , Chemical Abstract of Planta 1978, 139(2), 113–117.
Kida et al., *Relationship* . . . *and Plant Growth Regulating Activity of Amino Acid* . . . , Agr. Biol. Chem., 1976, 40(8), 1551–1557.

*Primary Examiner*—Richard L. Raymond
*Assistant Examiner*—Kristina Konstas
*Attorney, Agent, or Firm*—Armstrong, Nikaido, Marmelstein, Kubovcik & Murray

[57] ABSTRACT

A plant male sterilant which comprises as an active ingredient an effective amount of a threonine derivative having the formula (I):

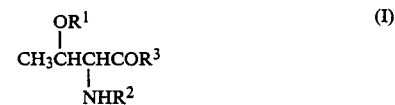

where $R^1$ is a $C_1$ to $C_2$ alkyl group; $R^2$ is a hydrogen atom, a $C_1$ to $C_3$ alkyl group or a group having the formula: $COR^4$ in which $R^4$ is a $C_1$ to $C_4$ alkyl group, a $C_1$ to $C_3$ alkoxy gruop, a phenyl group, an amino group or a $C_1$ to $C_3$ alkylamino group; $R^3$ is a hydroxy group, a $C_1$ to $C_4$ alkoxy group or a group having the formula: $NHR^5$ in which $R^5$ is a hydrogen atom, a hydroxy group, a $C_1$ to $C_3$ alkyl group, an amino group or a $C_1$ to $C_3$ alkylamino group and an inert carrier or diluent; a method for inducing male sterility in a plant which comprises applying the above plant male sterilant to the plant; and a method for producing hybrid seeds which comprises applying the above plant male sterilant to a female plant, and pollinating the female plant with pollens from a male plant. The plant male sterilant of the present invention can easily and efficiently induce male sterility in a plant without losing female fertility of the plant.

14 Claims, No Drawings

PLANT MALE STERILANT

BACKGROUND OF THE INVENTION

The present invention relates to a plant male sterilant which comprises as an active ingredient an effective amount of a threonine derivative having the formula (I):

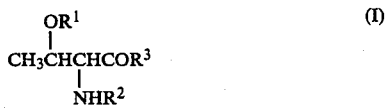

wherein $R^1$ is a $C_1$ to $C_2$ group; $R^2$ is a hydrogen atom, a $C_1$ to $C_3$ alkyl group or a group having the formula: $COR^4$ in which $R^4$ is a $C_1$ to $C_4$ alkyl group, a $C_1$ to $C_3$ alkoxy group, a phenyl group, an amino group or a $C_1$ to $C_3$ alkylamino group; $R^3$ is a hydroxy group, a $C_1$ to $C_4$ alkoxy group or a group having the formula: $NHR^5$ in which $R^5$ is a hydrogen atom, a hydroxy group, a $C_1$ to $C_3$ alkyl group, an amino group or a $C_1$ to $C_3$ alkylamino group and an inert carrier or diluent.

In recent years, the production of hybrid seeds has attracted attention.

It is known that the first filial generation plant has many outstanding characters such as an increased yield compared with its parent variety, owing to its vigorous growth. In order to obtain hybrid seeds it is necessary to prevent self-pollination of a female parent and stamens of the female parent have to be removed for that purpose.

Hitherto, there have been made a lot of efforts for the operation of removing stamens, i.e. castration, and also, since grains having a high rate of self-pollination, e.g. rice, wheat, and the like, have both stamens and pistils in small spikelet, it has been almost impossible to produce a large quantity of the hybrid seeds manually. There are another methods such as use of a cytoplasmic male sterility, but this method has problems such as it takes a long time for its breeding. Therefore, in recent years, it has been desired to develop simple and sure methods to induce male sterility in plant without losing pollination ability of the female parent.

Although O-methylthreonine is described in Winitz et al, J. Am. Chem. Soc. 78, 2423 (1956) and some derivatives thereof are also known, the male sterility inducing activity of O-methylthreonine and its derivatives has not been known at all.

As the result of the continuous effort of the present inventors, now it has been found that a compound having the formula (I) can induce the male sterility in a plant very simply and efficiently by treating the plant with the compound. Consequently the present invention is accomplished.

SUMMARY OF THE INVENTION

According to the present invention, there is provided a plant male sterilant which comprises as an active ingredient an effective amount of a threonine derivative having the formula (I) and an inert carrier or diluent; a method for inducing male sterility in a plant, which comprises applying an effective amount of a compound having the formula (I) and an inert carrier or diluent to the plant; and a method for producing seeds of the first filial generation, which comprises applying an effective amount of a compound having the formula (I) and an inert carrier or diluent to a female plant, and pollinating the female plant with pollens from a male plant.

DETAILED DESCRIPTION

Hereinafter, the present invention is explained in detail.

Among threonine derivatives used in the plant male sterilant of the present invention, L-isomers are preferable for their efficacy.

Also, among threonine derivatives used in the plant male sterilant of the present invention, threonine derivatives having the formula (I) in which $R^2$ is a hydrogen atom, a group having the formula: $COR^4$ in which $R^4$ is a $C_1$ to $C_4$ alkyl group, a $C_1$ to $C_3$ alkoxy group or a phenyl group, and $R^3$ is a hydroxy group or a $C_1$ to $C_4$ alkoxy group are preferable for their efficacy. More preferred are those in which $R^1$ is a methyl group; $R^2$ is a hydrogen atom, a group having the formula: $COR^4$ in which $R^4$ is a $C_1$ to $C_3$ alkoxy group or a phenyl group; and $R^3$ is a hydroxy group.

The plant male sterilant of the present invention is used for various cultivated plants, for instance, grains such as rice, wheat, barley, wild oats, rye and corn, leguminous crops such as soybean, vegetables such as eggplant, tomato, carrot and cabbage or flower and ornamental plants such as morningglory, petunia and zinnia. The plant male sterilant can sufficiently induce male sterility in a plant without causing any serious phytotoxicity on the plant.

That is to say, when the plant male sterilant of the present invention is used, it can induce almost complete male sterility in a plant without causing any undesirable side-effects on the plant.

Further, as mentioned in the following Test Examples, since the plant male sterilant of the present invention has no harmful influence on a pistil, the hybrid seeds can be easily obtained by means of crosspollination.

The threonine derivatives used as an active ingredient in the plant male sterilant of the present invention can be prepared according to a known method.

The O-alkylthreonines were prepared from threonine according to the procedure of K. Barlos and coworkers (Tetrahedron 39, 475 (1983)).

The N-acyl compounds are readily prepared from O-alkylthreonine under Schotten-Baumann conditions. And N-carbamoyl compounds are prepared for O-alkylthreonine by reaction with isocyanate in the presence of an amine.

Typical examples of the compound contained in the plant male sterilant of the present invention, which can be prepared though the above procedures, are shown in Table 1.

TABLE 1

$$\begin{array}{c} OR^1 \\ | \\ CH_3CHCHCOR^3 \\ | \\ NHR^2 \end{array} \quad (I)$$

| $R^1$ | $R^2$ | $R^3$ |
| --- | --- | --- |
| CH₃ | H | OH |
| " | COCH₃ | " |
| " | " | OCH₃ |
| " | COC₆H₅ | OH |
| " | " | OCH₃ |
| " | COOC₂H₅ | OH |
| " | " | OCH₃ |
| " | CONHC₂H₅ | OH |
| " | " | OCH₃ |

TABLE 1-continued $$\begin{array}{c} OR^1 \\ | \\ CH_3CHCHCOR^3 \\ | \\ NHR^2 \end{array} \quad (I)$$

| $R^1$ | $R^2$ | $R^3$ |
|---|---|---|
| " | $CH_3$ | OH |
| " | H | $NH_2$ |
| " | " | $NHCH_3$ |
| " | " | $NHNH_2$ |
| " | " | NHOH |
| $C_2H_5$ | " | $NH_2$ |
| $CH_3$ | " | $NHNHC_2H_5$ |
| $C_2H_5$ | " | $OC_2H_5$ |
| $CH_3$ | $CONH_2$ | $NH_2$ |

Compounds used in Test Examples are shown in Table 2. Compound No. 1 in Table 2 is a commercially available compound from Sigma Chemical Company. Compound No. 2 was prepared according to the process described in Tetrahedron 39, 475 (1983). Compound Nos. 3, 4 and 7 were prepared by reacting Compound No. 1 with an acylating agent in an aqueous alkali solution. Compound No. 8 was prepared by esterification of Compound No. 1 with thionylchloride in ethanol. Compound Nos. 5 and 6 were prepared by acylation or urea-formation of Compound No. 8, similarly to the above. Compound No. 9 was prepared from threonines having corresponding configuration according to the process described in Tetrahedron 39, 475 (1983).

TABLE 2

$$\begin{array}{c} OR^1 \\ | \\ CH_3CHCHCOR^3 \\ | \\ NHR^2 \end{array} \quad (I)$$

| Compound No. | $R^1$ | $R^2$ | $R^3$ | configuration | |
|---|---|---|---|---|---|
| 1 | $CH_3$ | H | OH | L | available from Sigma Chemical Company |
| 2 | $C_2H_5$ | " | " | " | $[\alpha]_D^{23}$ −48.0° (c = 1, $H_2O$) mp 217–218.5° C. |
| 3 | $CH_3$ | $COCH_3$ | " | " | $n_D^{23}$ 1.4667 |
| 4 | " | $COC_6H_5$ | " | " | mp 127–129° C. |
| 5 | $CH_3$ | $COCH_3$ | $OC_2H_5$ | " | mp 52–53° C. |
| 6 | " | $CONHC_2H_5$ | $OC_2H_5$ | " | mp 90–91° C. |
| 7 | $CH_3$ | $COOC_2H_5$ | OH | L | mp 43–45° C. |
| 8 | " | H | $OC_2H_5$ | " | $n_D^{23}$ 1.4289 |
| 9 | " | " | " | D-allo | $[\alpha]_D^{23}$ −8.1° (c = 0.68, $H_2O$) |

Hereinafter, the method of the present invention for inducing male sterility in a plant is explained.

On the practical usage of the compounds as described above as an active ingredient of the plant male sterilant of the present invention, they can be applied in conventional preparation forms such as an emulsifiable concentrate, a wettable powder, a flowable, a granule and a water-soluble solution in combination with a conventional solid carrier, liquid carrier, surface active agent or an auxiliary substance for formulation.

The content of the compounds of the present invention as the active ingredient in such preparations is within a range of 1 to 80% by weight, preferably 2 to 70% by weight.

Examples of the solid carrier, for instance, are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc.

As the liquid carrier, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethylsulfoxide, N,N-dimethylformamide, acetonitrile, water, etc.

Examples of the surface active agent used for emulsification, dispersion or spreading are, for instance, anionic type agents (e.g. alkylsulfates, alkylsulfonates, alkylarylsulfonates, dialkylsulfosuccinates, polyoxyethylenealkylaryl ether phosphates), non-ionic type agents (e.g. polyoxyethylene alkyl ethers, polyoxyethylene alkylaryl ethers, polyoxyethylene polyoxypropylene block copolymer, sorbitan fatty acid esters, polyoxyethylene sorbitan fatty acid esters), etc.

Examples of the auxiliary substance for formulation include ligninsulfonates, sodium alginate, polyvinyl alcohol, gum arabic, CMC (carboxymethyl cellulose), PAP (isopropyl acid phosphate), etc.

The compounds according to the present invention are usually formulated and applied to the plant by foliar treatment, soil treatment or application on the surface of the water during the period beginning just before the reproductive growth to the period of flowering.

As for the application on the surface of the water, it is necessary to partition a male plant and a female plant, which are planted adjoining each other, so that the male sterilant is not absorbed by the male plant.

As for the foliar treatment and soil treatment, it is also necessary to keep the male sterilant off the male plant.

In case of using the compounds as an active ingredient of the plant male sterilant, the dosage rate thereof varies depending on weather conditions, formulation used, application timing, application method, soil involved, species or varieties of the plants treated, etc. Generally, however, the dosage rate is from 50 to 10,000 grams, preferably from 100 to 5,000 grams, of the active ingredient per ha.

The plant male sterilant of the present invention formulated in the form of an emulsifiable concentrate, a wettable powder, a flowable or a watersoluble solution is ordinarily employed by diluting it with water at a volume of 1 to 10 liters per are, if necessary, with addition of auxiliary substances such as spreading agents.

On the other hand, the plant male sterilant formulated in the form of granules may be normally applied without dilution.

Examples of the spreading agent include, in addition to the surface active agents as noted above, polyoxyethylene resin acid (ester), ligninsulfonate, abietic acid salt, dinaphthylmethanedisulfonate, paraffin, etc.

Further, the compounds of the present invention may be applied in combination with plant growth regulators, herbicides, insecticides, acaricides, nematocides, fungicides, fertilizers, soil improvers, etc.

Furthermore, the sterilant of the present invention can be applied several times to the same plant by changing the application timing.

In order to obtain a lot of hybrid seeds, it is applicable to employ a method as follows:

Two parent plants are planted alternately. A number of ridges or a width thereof of each parent plant varies depending on species or varieties of the plant treated, environmental conditions, etc. After applying the plant male sterilant of the present invention to female plant, the female plant, which is already male sterilized, are pollinated with pollens of male plant carried by wind, insects, etc, and thereby the hybrid seeds can be obtained.

As another method for obtaining hybrid seeds of the first filial generation, methods such as the following method are also applicable. That is, a male plant and a female plant are separately planted. The female plant is treated with a plant male sterilant. After flowering, pollens are collected from the male plant, and the female plant is artificially pollinated with the pollens collected from the male plant.

Practical embodiments of preparation of the plant male sterilant of the present invention are illustratively shown in the following Formulation Examples wherein all parts are by weight. The compound number of the active ingredient corresponds to the one in Table 2.

FORMULATION EXAMPLE 1

Fifty parts of any one of Compound Nos. 1 to 9, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Ten parts of any one of Compound Nos. 5, 6 and 8, 14 parts of polyoxyethylenestyrylphenyl ether, 6 parts of calcium dodecylbenzenesulfonate and 70 parts of xylene are well mixed to obtain an emulsifiable concentrate.

FORMULATION EXAMPLE 3

Two parts of any one of Compound Nos. 1 to 9, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of any one of Compound Nos. 5, 6 and 8 is mixed with 3 parts of polyoxyethylene sorbitan monooleate, 3 parts of carboxymethyl cellulose and 69 parts of water and pulverized until the particle size of the mixture becomes less than 5 microns to obtain a flowable.

FORMULATION EXAMPLE 5

Three parts of any one of Compound Nos. 1 to 9, 1 part of polyoxyethylenestyrylphenyl ether and 96 parts of water are well mixed to obtain a liquid formulation.

The biological data of the compounds as the active ingredient in the plant male sterilant of the present invention are shown in the following Test Examples, wherein the compound number of the active ingredient corresponds to the one in Table 2.

TEST EXAMPLE 1

[Male sterility and female fertility test of wheat]

Plastic pots (volume: 200 ml) were filled with artificial soil mix and seeds of wheat (variety: NORIN No.61) and were sowed therein and grown in a greenhouse under the conditions of a day length of 15 hours and a temperature of 27° C. (day) and 20° C. (night).

A designed amount of the test compound formulated in a water-soluble solution was diluted with water containing a spreading agent, and the dilution was sprayed over the foliage of the test plants by means of a small hand sprayer at a spray volume of 1,000 liters per hectare once to a pot at 17 days before the first heading time of the test plant.

After the heading and flowering, artificial pollination was carried out as to 2 heads per pot of the pots which appeared to be sterile, using pollens obtained from the heads of untreated plants.

After ripening, there were harvested 4 heads per pot of no artificial pollination and 2 heads per pot of artificial pollination and each of spikelets and seeds thereof were counted.

The test was carried out in one pot per treatment.

The sterility rate and fertility rate was calculated according to the following expression:

Sterility Rate $(\%) = (1 - B/A) \times 100$

Fertility Rate $(\%) = (B/A) \times 100$

A: the number of seeds per spikelet of an untreated plant

B: the number of seeds per spikelet of a treated plant

Phytotoxicity to the shoots and heads was observed with the naked eye and rated with 5 indexes, i.e. $-$, $\pm$, $+$, $++$ and $+++$, in which the index "$-$" indicates that no or almost no difference was recognized between the test plant and a plant which was not treated with the plant male sterilant, and the index "$+++$" indicates that the test plant was withered or the growth of the test plant was completely inhibited. The results are shown in Table 3. In Table 3, "Sterility" is the sterility rate of no artificial pollination heads, and "Fertility" is the fertility rate of artificial pollination heads.

TABLE 3

| Compound No. | Dosage (g/ha) | Sterility (%) | Fertility* (%) | Phytotoxicity Shoot | Phytotoxicity Head |
|---|---|---|---|---|---|
| 1 | 1,000 | 98.3 | 67.8 | — | — |
|   | 4,000 | 100  | —    | ± | ± |

*Untreated plant was hand-emasculated.

TEST EXAMPLE 2

[Male sterility and female fertility test of morningglory]

Plastic pots (volume: 200 ml) were filled with plow-field soil and seeds of morningglory were sowed therein and growth under the same conditions as in Test Example 1 for 7 days. After that, there was carried out a short day treatment (22° C., day length of 8 hours) in a growth chamber for 14 days. After the short day treatment, the test plant was replaced under the same conditions as in Test Examples 1.

A designed amount of the test compound was sprayed over the foliage of the test plants according to the same methods as in Test Example 1 once to a pot at 15 days before the first flowering time of the test plant. The test was carried out in two pots per treatment.

After flowering, seven flowers per treatment were observed visually and rated with the following index.

Effect to the anther

A: No anther dehiscence

B: Anther dehiscence, few pollen number

C: Anther dehiscence, normal pollen number

Phytotoxicity to the shoots and whole flowers was observed in a similar manner as in Test Example 1.

And artificial pollination by untreated pollen was carried out to the flower of which the effect to the anther was index A.

After seed set, the number of seed set flowers were counted and the fertility rate was calculated according to the following expression:

Fertility rate (%) =

$$\frac{\text{the number of seed set flowers}}{\text{the number of artificially pollinated flowers}} \times 100$$

The results are shown in Table 4.

TABLE 4

| Compound No. | Dosage (g/ha) | Effect to* the anther A B C | Phytotoxicity Shoot Flower | Fertility rate (%) |
|---|---|---|---|---|
| 1 | 4000 | 6  1  0 | —    — to ± | 60 |

*Number of flowers rated as A, B or C

TEST EXAMPLE 3

[Male sterility and female fertility test of rice plant]

Plastic pots (volume: 200 ml) were filled with artificial soil mix and seeds of rice were sowed therein and grown under the same conditions as in Test Example 1.

Pots were flooded and then the test compound was sprayed over the foliage of the test plants according to the same methods as in Test Example 1 once to a pot at 18 days before the first heading time of the test plants.

The test was carried out in two pots per treatment.

After flowering, the test plants in 1 pot out of 2 pots were artificially pollinated with pollenes obtained from heads not treated with plant male sterilant.

After ripening, there were harvested 4 heads per pot and glumous flower and seeds were counted.

The sterility rate of no artificial pollination heads was calculated according to the following expression:

Sterility rate (%) = $(1 - B/A) \times 100$

A: the number of seeds per glumous flower of an untreated plant

B: the number of seeds per glumous flower of a treated plant

Phytotoxicity to the shoots and heads was observed in a similar manner as in Test Example 1.

The results were shown in Table 5.

Compound No. 1 gave a high sterility rate at a dosage of 200 g/ha and 400 g/ha in the test plants which were not artificially pollinated. On the other hand, in the artificially pollinated plants, considerable fertility was shown. That is, it was found that the test plant had female fertility when it is treated with Compound No. 1 at a dosage at which male sterility was shown. Further, phytotoxity observed was little.

TABLE 5

| Compound No. | Dosage (g/ha) | Sterility Rate (%) | Phytotoxicity Shoot | Head |
|---|---|---|---|---|
| 1 | 200 | 92.8 | ± | — |
|   | 400 | 99.0 | ± | — |

Test Example 4

[Sterility test of wheat]

Wheat were grown according to the same method as in Test Example 1.

A designed amount of the test compounds was sprayed over the foliage of the test plants according to the same methods as in Test Example 1 once to a pot at 15 days before the first heading time of the test plant.

After ripening, there were harvested 4 heads per pot and each of spikelets and seeds thereof were counted.

The test was carried out in one pot per treatment.

The sterility rate was calculated according to the same methods as in Test Example 1.

The results are shown in Table 6.

TABLE 6

| Compound No. | Dosage (g/ha) | Sterility rate (%) |
|---|---|---|
| 2 | 1000 | 100 |
| 3 | 1200 | 96.2 |
| 4 | 250 | 100 |
| 5 | 1000 | 100 |
| 6 | 1000 | 100 |
| 7 | 250 | 98.3 |
| 8 | 500 | 95.4 |

TEST EXAMPLE 5

[Male sterility and female fertility test of wheat]

Wheat were grown according to the same methods as in Test Example 1.

A designed amount of the test compounds was sprayed over the foliage of the test plants according to the same methods as in Test Example 1 three times to the same pot, i.e. 22 days before, 15 days before and 8 days before the first heading time of the test plant.

After the heading and flowering, artificial pollination was carried out as to 4 heads per pot of the pots which appeared to be sterile, using pollens obtained from the heads of untreated plants.

After ripening, there were harvested 4 heads per pot of no artificial pollination and 4 heads per pot of artificial pollination and each of spikelets and seeds thereof was counted.

The test was carried out in one pot per treatment.

The sterility rate and fertility rate was calculated according to the same methods as in Test Example 1.

The results are shown in Table 7. In Table 7, "Sterility" is the sterility rate of no artificial pollination heads, and "Fertility" is the fertility rate of artificial pollination heads.

TABLE 7

| Compound No. | Dosage (g/ha) | Sterility (%) | Fertility* (%) |
|---|---|---|---|
| 5 | 1000 | 100 | 70.6 |
| 6 | 1000 | 100 | 77.3 |

*Untreated plant was handemasculated

TEST EXAMPLE 6

[Sterility test of rice plant]

Plastic pots (volume: 200 ml) were filled with artificial soil mix and seeds of rice were sowed therein and grown under the same conditions as in Test Example 1. Pots were flooded and then a designed amount of the test compounds were sprayed over the foliage of the test plants according to the same methods as in Test Example 1 once to a pot at 14 days before the first heading time of the test plants.

The test was carried out in one pot per treatment.

After ripening, there were harvested 4 heads per pot and glumous flower and seeds were counted.

The sterility rate was calculated according to the same method as Test Example 3.

The results are shown in Table 8.

TABLE 8

| Compound No. | Dosage (g/ha) | Sterility rate (%) |
|---|---|---|
| 2 | 1000 | 100 |
| 3 | 1200 | 100 |
| 4 | 250 | 98.2 |
| 5 | 1000 | 100 |
| 7 | 250 | 100 |
| 8 | 1000 | 100 |
| 9 | 1000 | 100 |

TEST EXAMPLE 7

[Male sterility and female fertility test of rice plant]

Plastic pots (volume: 200 ml) were filled with artificial soil mix and seeds of rice were sowed therein and grown under the same conditions as in Test Example 1.

Pots were flooded and then a designed amount of the test compounds was sprayed over the foliage of the test plants according to the same methods as in Test Example 1 three times to the same pot, i.e. 21 days before, 14 days before and 7 days before the first heading time of the test plant.

The test was carried out in one pot per treatment.

After the heading and flowering, artificial pollination was carried out as to 2 heads per pot of the pots which appeared to be sterile, using pollers obtained from the heads of untreated plants.

After ripening, there were harvested 4 heads per pot of no artificial pollination and 2 heads per pot of artificial pollination and glumous flower and seeds were counted. The male sterility rate of no artificial pollination heads and the female fertility rate of artificial pollination heads were calculated according to the following expression.

Sterility rate (%) of no artificial pollination heads
= $(1 - B/A) \times 100$

Fertility rate (%) of artificial pollination heads
= $B/A \times 100$

A: the number of seeds per glumous flower of an untreated plant.

B: the number of seeds per glumous flower of a treated plant.

The results are shown in Table 9.

In Table 9, "Sterility" is the sterility rate of no artificial pollination heads, and "Fertility" is the fertility rate of artificial pollination heads.

TABLE 9

| Compound No. | Dosage (g/ha) | Sterility (%) | Fertility* (%) |
|---|---|---|---|
| 4 | 500 | 100 | 71.8 |
| 7 | 500 | 100 | 69.5 |

*Untreated plant was handemasculated.

In addition to the ingredients used in the Formulation Examples and Test Examples, other ingredients can be used in the Formulation Examples and Test Examples as set forth in the specification to obtain substantially the same results.

What we claim is:

1. A plant male sterilant which comprises as an active ingredient an effective amount of a threonine derivative having the formula (I):

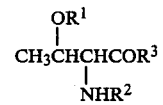

wherein $R^1$ is a $C_1$ to $C_2$ alkyl group; $R^2$ is a hydrogen atom, a $C_1$ to $C_3$ alkyl group or a group having the formula: $COR^4$ in which $R^4$ is a $C_1$ to $C_4$ alkyl group, a $C_1$ to $C_3$ alkoxy group, a phenyl group, an amino group or a $C_1$ to $C_3$ alkylamino group; $R^3$ is a hydroxy group, a $C_1$ to $C_4$ alkoxy group or a group having the formula: $NHR^5$ in which $R^5$ is a hydrogen atom, a hydroxy group, a $C_1$ to $C_3$ alkyl group, an amino group or a $C_1$ to $C_3$ alkylamino group and an inert carrier or diluent.

2. The plant male sterilant of claim 1, wherein said threonine derivative has L-configuration.

3. The plant male sterilant of claim 1, wherein $R^1$ is a $C_1$ to $C_2$ alkyl group; $R^2$ is a hydrogen atom, a group having the formula: $COR^4$ in which $R^4$ is a $C_1$ to $C_4$ alkyl group, a $C_1$ to $C_3$ alkoxy group or a phenyl group; and $R^3$ is a hydroxy group or a $C_1$ to $C_4$ alkoxy group.

4. The plant male sterilant of claim 1, wherein $R^1$ is a methyl group; $R^2$ is a hydrogen atom, a group having the formula: $COR^4$ in which $R^4$ is a $C_1$ to $C_3$ alkoxy group or a phenyl group; and $R^3$ is a hydroxy group.

5. A plant male sterilant which comprises an effective amount of O-methylthreonine as an active ingredient and an inert carrier or diluent.

6. A plant male sterilant which comprises an effective amount of L-O-methylthreonine as an active ingredient and an inert carrier or diluent.

7. A plant male sterilant which comprises an effective amount of L-N-benzoyl-O-methylthreonine as an active ingredient and an inert carrier or diluent.

8. A plant male sterilant which comprises an effective amount of L-N-ethoxycarbonyl-O-methylthreonine as an active ingredient and an inert carrier or diluent.

9. A method for inducing male sterility in a plant, which comprises applying an effective amount of a threonine derivative having the formula (I):

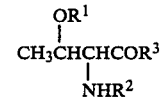

wherein $R^1$ is a $C_1$ to $C_2$ alkyl group; $R^2$ is a hydrogen atom, a $C_1$ to $C_3$ alkyl group or a group having the formula: $COR^4$ in which $R^4$ is a $C_1$ to $C_4$ alkyl group, a $C_1$ to $C_3$ alkoxy group, a phenyl group, an amino group or a $C_1$ to $C_3$ alkylamino group; $R^3$ is a hydroxy group, a $C_1$ to $C_4$ alkoxy group or a group having the formula: $NHR^5$ in which $R^5$ is a hydrogen atom, a hydroxy group, a $C_1$ to $C_3$ alkyl group, an amino group or a $C_1$ to $C_3$ alkylamino group and an inert carrier or diluent to the plant.

10. A method for inducing male sterility in a plant, which comprises applying an effective amount of O-methylthreonine and an inert carrier or diluent to the plant.

11. A method for inducing male sterility in a plant, which comprises applying an effective amount of L-O-methylthreonine and an inert carrier or diluent to the plant.

12. The method of claim 9, in which the plant is rice plant or wheat.

13. The method of claim 10, in which the plant is rice plant or wheat.

14. A method for producing hybrid seeds of the first filial generation, which comprises applying an effective amount of a threonine derivative having the formula (I):

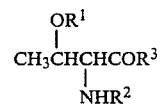

wherein $R^1$ is a $C_1$ to $C_2$ alkyl group; $R^2$ is a hydrogen atom, a $C_1$ to $C_3$ alkyl group or a group having the formula: $COR^4$ is which $R^4$ is a $C_1$ to $C_4$ alkyl group, a $C_1$ to $C_3$ alkoxy group, a phenyl group, an amino group or a $C_1$ to $C_3$ alkylamino group; $R^3$ is a hydroxy group, a $C_1$ to $C_4$ alkoxy group or a group having the formula: $NHR^5$ in which $R^5$ is a hydrogen atom, a hydroxy group, a $C_1$ to $C_3$ alkyl group, an amino group or a $C_1$ to $C_3$ alkylamino group and an inert carrier or diluent to a female plant, and pollinating the female plant with pollens from a male plant.

* * * * *